(12) United States Patent
Sommacal

(10) Patent No.: US 10,239,188 B2
(45) Date of Patent: Mar. 26, 2019

(54) METHOD OF CLEANING AND SANITIZING MEDICAL INSTRUMENTS AND ACCESSORIES AND APPARATUS THEREFOR

(71) Applicant: Alessandro Paolo Sommacal, Padua (IT)

(72) Inventor: Alessandro Paolo Sommacal, Padua (IT)

(73) Assignee: BICAR JET S.R.L., Padua (IT)

( * ) Notice: Subject to any disclaimer, the term of this patent is extended or adjusted under 35 U.S.C. 154(b) by 0 days.

(21) Appl. No.: 14/953,402

(22) Filed: Nov. 29, 2015

(65) Prior Publication Data

US 2016/0081756 A1    Mar. 24, 2016

Related U.S. Application Data

(63) Continuation-in-part of application No. 14/342,353, filed as application No. PCT/IB2012/051514 on Mar. 29, 2012, now abandoned.

(30) Foreign Application Priority Data

Nov. 11, 2011    (IT) .............. PD2011A0352

(51) Int. Cl.
*B24C 11/00*   (2006.01)
*B24C 1/00*    (2006.01)
*B24C 3/04*    (2006.01)
*A61B 90/70*   (2016.01)
*A61B 19/00*   (2006.01)

(52) U.S. Cl.
CPC ............ *B24C 11/005* (2013.01); *A61B 19/34* (2013.01); *A61B 90/70* (2016.02); *B24C 1/00* (2013.01); *B24C 3/04* (2013.01); *A61B 2090/701* (2016.02)

(58) Field of Classification Search
None
See application file for complete search history.

(56) References Cited

U.S. PATENT DOCUMENTS 5,591,064 A * 1/1997 Spears, Jr. ............ B24C 7/0053
                                             451/100
7,249,994 B2 * 7/2007 Sommacal .............. B24C 1/003
                                             451/88

(Continued)

FOREIGN PATENT DOCUMENTS

EP    1683499 A1 *  7/2006    ........... A61C 19/002
JP    11207609 A  *  8/1999

OTHER PUBLICATIONS

English Machine Translation of EP 1683499 A1, obtained Sep. 2017.*

(Continued)

*Primary Examiner* — Nicole Blan
(74) *Attorney, Agent, or Firm* — Themis Law

(57) ABSTRACT

A method of cleaning and sanitizing surgical tools or surgical instruments and accessories in general, and a device configured to implement the method. The method includes the use of a an abrasive cleaning material, which is emitted under pressure and at high speed to abrade and remove substances that adhere to the surfaces of the instruments and accessories, and the pressure of which can be regulated according to the type of surface to be cleaned.

12 Claims, 1 Drawing Sheet

(56) References Cited

U.S. PATENT DOCUMENTS

| | | | | |
|---|---|---|---|---|
| 2003/0012978 A1* | 1/2003 | Sodani | ............... | B24C 1/06 |
| | | | | 428/659 |
| 2006/0062820 A1* | 3/2006 | Gertner | ............... | A61L 27/54 |
| | | | | 424/422 |
| 2009/0104582 A1* | 4/2009 | Duncan | ............... | A61C 8/0089 |
| | | | | 433/173 |
| 2013/0171023 A1* | 7/2013 | Ben-Shmuel | ............... | A47L 15/4236 |
| | | | | 422/22 |

OTHER PUBLICATIONS

English Machine Translation of JP 11-207609 A, obtained Sep. 2017.*

* cited by examiner

METHOD OF CLEANING AND SANITIZING MEDICAL INSTRUMENTS AND ACCESSORIES AND APPARATUS THEREFOR

FIELD OF THE INVENTION

The present patent concerns the processes and devices for cleaning medical instruments and accessories, and in particular it concerns a new sand blasting process for cleaning and sanitizing medical instruments and accessories, in particular surgical instruments, and apparatus therefor.

BACKGROUND OF THE INVENTION

Surgical tools and instruments used in the medical field, for example in surgery, dentistry, veterinary medicine, etc, are known, which are used for carrying out operations on the patient's body.

In order to be used, said instruments must be completely and accurately cleaned and sanitized, meaning that their surface must not present any type of foreign substance, bacteria or other elements that may cause pathological reactions in any type of patient.

Therefore, surgical tools must be cleaned again and sanitized accurately after each use, as well as packaged individually in sterile and sealed packages suited to be quickly opened to extract the tools at the moment of use by the surgeon or operator in general.

In particular, before undergoing the sanitization process, which usually is performed with high temperature steam or other chemical or thermal systems, the surgical instruments must be previously cleaned very accurately in order to completely remove any organic residues from their metal surface.

It is in the organic residues, in fact, if they are not removed before sanitization, that the molecule breaking process takes place during the heat treatment, with the formation of substances that affect the cleanliness and sterility of the surgical instrument and considerably increase corrosion problems.

In order to protect the health of medical personnel against possible infections due to contact, even if accidental, with infected surgical instruments, automatic instrument washing devices have been designed that are used for cleaning and sanitizing the instruments.

These devices usually operate in three steps. During the first step the surgical instruments are washed with suitable detergents and rinsed with water, which must ensure complete removal of the organic residues present on the instruments.

A drawback posed by the known processes using chemical products lies in that some of them, commonly used in washing cycles, are too aggressive against the stainless steel used for making surgical instruments and cause these to corrode.

Furthermore, the surgical instruments comprise portions of their surface that are smooth and other portions that are rough, for example at the level of the handpieces, where better hold must be guaranteed to the operator. Some surgical instruments also comprise interstices and small spaces according to the specific shape of the instrument and to usage needs.

Organic impurities accumulate in said interstices and on said rough surface and are difficult to remove with the known washing processes.

Due to the fact that the cleansing systems used are not perfectly effective, before the washing operations a manual mechanical operation is often necessary and this must be performed by a specialized operator. This operation consists in the manual brushing of the instruments, which subjects the operator to the risk of infections, due to possible cuts, abrasions, punctures or any other accidental event deriving from the brushing operation. Furthermore, the brushing operation does not always guarantee the complete removal of organic residues, since the tools used for this mechanical operation cannot always reach the contaminated interstices or cavities and/or sometimes the encrustation resulting from the drying of the organic substances are especially adherent to the surface.

For this reason systems are also known that use softening baths suited to favor the mechanical and/or chemical removal of organic residues from the most complex surfaces, however these methods are not always effective. The contaminations left, especially in the interstices and cavities, are then fixed with the sanitizing heat treatment and therefore the effectiveness of this last step, so important for the health of the patients that will be treated subsequently, cannot be guaranteed.

The second, neutralizing step, includes the use of acid products that serve to solubilize and completely remove the oxides formed during cleaning with detergents.

The acid solutions used, however, have also a corrosive effect, in particular at the level of the contact points between metal and metal or between metal and plastic, where the conditions may facilitate the occurrence of localized corrosion phenomena.

The third step includes the cleansing of the instruments with high temperature water, approximately at 90°, which may cause more marked corrosion effects at the level of said areas subjected to localized corrosion.

Therefore, the known processes and equipment for cleaning and sanitizing surgical instruments pose several drawbacks.

SUMMARY OF THE INVENTION

In order to overcome said drawbacks, a new type of sand blasting process has been studied and implemented, which uses a saline compound for cleaning and sanitizing surgical tools or surgical instruments in general, in addition to a device for implementing said process. In one embodiment, the saline compound is or contains sodium bicarbonate.

The main advantage of the present invention is to ensure highly effective mechanical removal of the substances stuck to the entire surface of the instruments and, at the same time, a highly effective washing, sanitizing and disinfecting process, if any.

Another advantage of the present invention to guarantee a long-lasting disinfecting and anti-bacterial action, intended to hinder a new proliferation of bacteria on the surfaces of the instruments.

A further important advantage of the present invention consists in the considerable reduction of cleaning times and thus of the related costs, as the new product performs the abrading step, the cleansing step and if necessary also the disinfecting and/or biocidal action at the same time, with a single application.

Another aspect deriving from the use of the present invention lies in the reduction of energy costs, as the effectiveness of the product is guaranteed even if the product is applied with air, with or without water, not heated, and thus with no need to use hot water.

Endoscopy is known and widely used, both for diagnostic and therapeutic purposes, and requires endoscopic instruments and accessories, which must be disinfected with a high level of cleaning and sterilization, because those instruments contact tissues that may be healthy but that sometimes have a low level of integrity.

Flexible endoscopic instruments may include non-metallic probes, which are typically made of plastic materials and which are commonly used in endoscopic applications.

Moreover, a variety of medical instruments and accessories have outer surfaces that exhibit cavities, depressions, areas of roughness, corrugations and other surface features that are particularly difficult to clean and sterilize with methods of the prior art.

It is an advantage of the present invention to provide an improved method of mechanical cleaning, such as sanding with a saline compound, for example with sodium bicarbonate, to clean and sterilize surgical tools or medical instruments in general, including endoscopic instruments and instruments having metallic and/or non-metallic surfaces, and an apparatus to perform the new method.

It is also an advantage of the present invention to maximize the efficiency of mechanic removal of attached substances from surfaces of instruments, especially of attached substances from surfaces that have specific shapes, or are threaded or provided with surface features such as surface treatments, cavities, corrugations or roughness areas of any dimensions.

Another aspect of the present invention is to provide a cleaning, sterilizing and antibacterial treatment, even long term, preventing a new bacterial proliferation on the surface of an instrument and also in surface features such as interspaces, cavities and/or concavities of the instrument, even of minimal dimensions.

Still another, important aspect of the present invention is achieving a remarkable decrease in washing time and, therefore, of the related costs, because the new method does not require additional operations, for example, manual operations, to clean interstices and cavities.

Yet another aspect of the present invention is to further limit the handling by operators of the surgical instruments or tools to be cleaned, thereby increasing operator safety.

These and other direct and complementary objects are achieved by the new sand blasting method, which uses sodium bicarbonate for cleaning and sanitizing surgical tools or surgical instruments in general, and by a device for implementing such method.

According to the new cleaning process, the removal of the substances adhering and stuck to the surfaces of the instrument to be cleaned takes place through abrasion, with the ejection of an abrasive cleaning material at high speed against the instruments to be cleaned.

In particular, said abrasive cleaning material comprises sodium bicarbonate salts, mixtures of the same or the like.

The sodium bicarbonate salts can be used both dry and wet, in the latter case dissolved in water beyond the saturation limit to provide a supersaturated solution, so as to form a solution comprising dissolved and undissolved salts, suited to be emitted under pressure and at high speed and ejected against the instruments to be cleaned. The portion of sodium bicarbonate salts dissolved in the solution performs the real washing function, dissolving and leaching the organic material present on the surface of the instruments.

The portion of undissolved sodium bicarbonate salts, instead, operates as an abrasive material.

The new process is particularly suitable for washing said medical instruments, in particular surgical instruments, as it does not involve any corrosive effect on the material from which said instruments are made and there is no abrasive action on the instrument, meaning no surface modification of the instrument.

Furthermore, sodium bicarbonate has a strong sanitizing, antibacterial and antifungal action.

Furthermore, sodium bicarbonate is not dangerous for operators and is not detrimental to the environment, is 100% biodegradable and soluble, which means that it is not polluting and not subjected to special restrictions for storage, transport and handling.

In one embodiment of the invention, the abrasive cleaning material comprises, in addition to sodium bicarbonate salts and water, one or more further disinfecting and/or biocidal agents, for example in a concentration included between 0.1 and 25% by weight.

This way, with a single step it is possible to carry out both the instrument washing operation and the disinfecting operation.

According to the invention, the abrasive cleaning material may also comprise one or more further substances with cleansing and/or disinfecting properties and/or one or more specifically acting medical products.

The water used may be heated or at room temperature, since the use of sodium bicarbonate, in particular with the addition of disinfecting and/or biocidal agents, guarantees optimal cleaning and sanitizing results.

Therefore, the new process also ensures savings in energy and running costs.

The elimination of the brushing process results in the elimination of the risks for operators deriving from possible infections due to accidental punctures, abrasions or cuts that may occur during the brushing operation, with a clear reduction of any accident related costs.

The improved effectiveness of the cleaning process also generates a considerable reduction in the percentage of infections in patients treated subsequently, thanks to better and more effective cleaning of the surgical instruments, with a consequent reduction of the related costs.

The process may comprise a final step in which the instruments are rinsed with cold water, meaning non heated water, and/or are blown with dry sodium bicarbonate salts.

DETAILED DESCRIPTION OF EMBODIMENTS OF THE INVENTION

Figure 1:
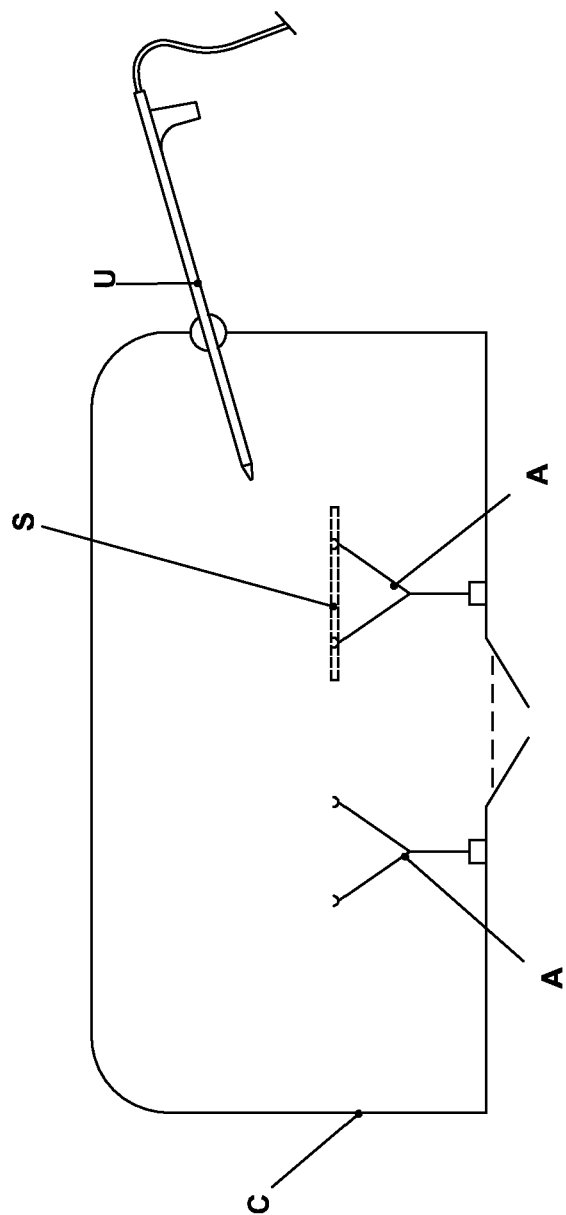
FIG. 1 illustrates a device according to the invention.

For the implementation of the new process for cleaning and sanitizing surgical instruments a device, shown in FIG. 1, is used that comprises a closed sand blasting cabinet (C) suited to accommodate one or more instruments to be cleaned.

According to the invention, inside said cabinet there is/are one or more supports (A) for said surgical instruments (S), suited to constrain the instruments and keep them in position during the sand blasting operation.

Said supports (A) can be of the fixed or movable type, for example they can be rotated or translated, so as to expose the entire surface of the instrument to the jet emitted by the emitter nozzle (U).

According to a possible embodiment of the invention, said emitter nozzle is movable, that is, travels along the three spatial directions and/or rotates, so as to direct the jet on the entire surface of the instruments to be cleaned. Said instruments to be cleaned can in turn be constrained to said fixed or movable supports, or held manually by the user.

Said emitter nozzle can be moved manually or can be automated.

According to a further alternative embodiment, said emitter nozzle is fixed inside the cabinet, and thus the jet is permanently oriented in the same direction. According to this solution, the instruments to be cleaned can be maneuvered manually by the operator, in order to expose their entire surface to the jet. Alternatively, said supports of the instruments to be cleaned are mechanized and movable, translating and/or rotating, thus completely automating the process.

The device also comprises at least one abrasive material feed system, in turn comprising an abrasive material tank, and wherein, through at least one duct, a flow of pressurized air and/or water draws or thrusts said abrasive material from said tank and transports it to an emitter nozzle located inside said cabinet.

By means of said emitter nozzle said abrasive material is ejected at high speed, inside said sand blasting cabinet, on said instruments to be cleaned. The device may also comprise a vacuum suction system for drawing the abrasive material inside said cabinet and an air filtering system for filtering the air flowing out of the cabinet and recovering the material used in at least one apposite container.

Said sand blasting cabinet can have any shape and size and comprises a casing with at least one access door for introducing and extracting the surgical instruments.

Said casing of the cabinet comprises also one or more check windows, one or two openings with sleeve glove suited to allow the operator to maneuver the sand blasting nozzle and/or to rotate the instruments to be cleaned inside the cabinet, and one discharge opening on the bottom of the cabinet.

Said bottom of the cabinet can be shaped, for example, so as to favor the outflow of the waste material.

The cleaning operations with sodium bicarbonate salts can thus be carried out inside said cabinet, both manually, by one or more operators at the same time, and in an automated manner, with the aid of appropriate instruments or suitable automated mechanical systems.

Pressure/Hardness

A key and peculiar feature of sodium bicarbonate is having a hardness that is much lower than sand.

Using the Mohs scale for an empiric evaluation of the hardness of materials, sodium bicarbonate lays between 2.5 and 3, while sand, which is composed prevalently of silica compounds, lays between 6 and 7.

Such hardness causes sand to affect the metal surface of surgical tools negatively. On the contrary, the abrasive action of sodium bicarbonate affects and removes all impurities that are disposed on the surgical tool and that have a lower hardness, but does not affects the metal surface, which has a higher hardness.

Moreover, by varying the ejection pressure of the sodium bicarbonate, even less resistant materials can be treated, for example, plastics.

A method according to the invention, therefore, include a step of regulating the ejection pressure of a saline compound or of the sodium bicarbonate, among other things, as a function of the hardness and granulometry of the bicarbonate.

Characteristic hardness and dimensions of agglomerates of sodium bicarbonate are indeed features that have a limited intrinsic variability, especially because of the speed of the production process of sodium bicarbonate.

In a method according to the invention, ejection pressure of the bicarbonate, and, accordingly, ejection speed, can be varied, for example, according to the type of object to be cleaned and of the material with which the object is made.

Such ejection pressure is preferably between 0.5 and 12 bars and can be adjusted even during the cleaning process.

In particular, when parts of plastic surgical instruments must be cleaned, ejection pressure is maintained between 0.5 and 3 bars, considering that the abrasive action must be limited to the impurities on the instrument without affecting the plastic layer.

Instead, when parts of steel surgical instruments must be cleaned, that pressure is kept between 1.5 and 8 bars due to the higher hardness of the metal surface.

Granulometry

A method according to the invention includes using one or more alkaline bicarbonate salts, such as $LiHCO_3$, $NaHCO_3$, $KHCO_3$, $NH_4HCO_3$, and/or one or more alkaline carbonate salts, such as $Li_2CO_3$, $Na_2CO_3$, $K_2CO_3$, $(NH_4)_2CO_3$), and/or chlorine salts, such as $NaCl$, $KCl$, $NH_4Cl$.

A cleaning step according to the invention includes removing substances that are attached or even strongly attached to the surfaces of an instrument by abrasion by emitting an abrasive cleaning material at high speed and with controlled granulometry against the instrument to be cleaned, and under conditions related to the type of surface to be cleaned.

In particular, the abrasive cleaning material may include a saline compound of sodium bicarbonate. "Compound" shall not imply here that the salts must be chemically bound to another substance, but, in one embodiment, they may be mixed therewith, for example, may be dissolved in water.

The un-dissolved portion of the sodium bicarbonate acts as an abrasive material.

A method according to the invention includes a first step of evaluating the surfaces to be treated and the dimensions of corrugations, cavities or areas of surface roughness in general, an a second step of evaluating the granulometry of the abrasive material to be utilized.

A method according to the invention may include two or more steps of selecting the granulometry to be utilized, and one or more steps of emitting the material with the selected granulometry. This enables the emission, in sequence or even contemporaneously, of materials having two or more different granulometries in order to further enhance cleaning effectiveness.

In particular, a method according to the invention of cleaning surgical tools and accessories with a saline compound of bicarbonate is particularly effective with an abrasive material having a granulometry between 10 and 700 µm.

When the surgical instruments have surfaces with corrugations, cavities, depressions and areas of surface roughness having dimensions generally between 50 and 250 µm, the saline compound containing sodium bicarbonate is of fine grade, that is, has a granulometry between 10 and 250 µm.

In a preferred embodiment, the compound containing sodium bicarbonate has a granulometry between 20 and 200 µm.

When the instruments to be cleaned have corrugations, cavities and areas of surface roughness with relevant dimensions larger than 250 µm, the saline compound containing sodium bicarbonate is of large grade, that is, has a granulometry between 10 and 700 µm.

In one embodiment, the saline compound containing sodium bicarbonate has a granulometry between 70 and 600 µm.

In one embodiment, the saline compound containing sodium bicarbonate has a granulometry between 150 and 500 μm.

Therefore, a method according to the invention is particularly suited for washing surgical tools having surfaces of any kind.

Device

In order to perform a method of cleaning and sterilizing surgical tools according to the invention, a device is provided having a closed sanding booth shaped to house one or more instruments to be cleaned.

A device according to the invention includes a system that emits an abrasive material into the booth and onto the instruments under pressure. The abrasive material includes that includes one or more saline compounds.

The device further includes a system that regulates the ejection pressure of the abrasive material between 0.5 and 12 bars. Examples of pressure regulators include valves that automatically cuts off flow at a certain pressure, flowmeters, rotometers or mass flow controllers.

In a preferred embodiment, a device according to the invention includes also a system that regulates the ejection pressure at preset values, for example between 0.5 and 3 bars to treat surgical instruments having plastic surfaces and between 1.5 and 8 bars to treat surgical instruments having metal surfaces.

The device may further include a feeding system of the abrasive material, which includes a storage tank for the abrasive material and from which, through a conduit, an air and/or water flow aspires or pushes the abrasive material from the tank and carries it to an emission nozzle disposed within the booth.

The abrasive material is emitted at high pressure from the nozzle into the booth for mechanical cleaning, such as sanding, onto the instruments to be cleaned.

In a preferred embodiment, the tank is removable in order to feed each time a saline compound containing sodium bicarbonate having a desired granulometry according to the instruments to be cleaned.

Alternatively, in one embodiment, the device may have two or more tanks, each containing the saline compound with the sodium bicarbonate having a determined granulometry. Each of those tanks is operatively coupled, or is selectively operatively coupled, to the emission nozzle, or to its own emission nozzle.

In one embodiment, the device includes one or more units that automatically select the tank, from which the abrasive material to be emitted is taken. Such selection may include an alternative or contemporaneous selection from those two or more tanks, in order to provide for an alternative or contemporaneous emission of a material having different granulometries.

While the invention has been described in connection with the above described embodiments, it is not intended to limit the scope of the invention to the particular forms set forth, but on the contrary, it is intended to cover such alternatives, modifications, and equivalents as may be included within the scope of the invention.

Further, the scope of the present invention fully encompasses other embodiments that may become obvious to those skilled in the art and the scope of the present invention is limited only by the appended claims.

With reference to the foregoing description, the following claims are expressed.

The invention claimed is:

1. A method of cleaning and sterilizing medical instruments or accessories, comprising:
providing an abrasive cleaning material; and
emitting the abrasive cleaning material under ejection pressure and at a predetermined speed against the medical instruments or accessories, thereby achieving a mechanical cleaning by abrading and removing adhered substances from surfaces of the medical instruments or accessories, wherein the abrasive cleaning material comprises a saline compound, and wherein the saline compound is ejected as a supersaturated solution;
regulating the ejection pressure of the abrasive cleaning material; and
rinsing the medical instruments or accessories in non-heated water.

2. The method of claim 1, wherein the regulating the ejection pressure comprises adjusting the ejection pressure comprises adjusting the ejection pressure between 0.5 and 12 bar according to a material or materials, with which the medical instruments or accessories are made.

3. The method of claim 2, wherein the adjusting the ejection pressure comprises adjusting the ejection pressure between 0.5 and 3 bars to treat plastic surfaces of the medical instruments or accessories.

4. The method of claim 2, wherein the adjusting the ejection pressure comprises adjusting the ejection pressure between 1.5 and 8 bars to treat metallic surfaces of the medical instruments or accessories.

5. The method of claim 1, wherein the saline compound has a predetermined granulometry based on a configuration of the medical instruments and accessories to be cleaned and of dimensions of depressions, cavities, interstices and roughness areas of surfaces of the medical instruments and accessories to be cleaned.

6. The method of claim 1, wherein the saline compound comprises an alkaline bicarbonate salt.

7. The method of claim 1, wherein the saline compound comprises a chlorine salt.

8. The method of claim 1, wherein the saline compound has a granulometry between 10 and 700 μm.

9. The method of claim 1, wherein the saline compound has a granulometry between 70 and 600 μm.

10. The method of claim 1, wherein the saline compound comprises has a granulometry between 150 and 500 μm.

11. The method of claim 1, further comprising:
selecting at least one granulometry of the abrasive cleaning material to be used; and
emitting the abrasive cleaning material with the selected at least one granulometry.

12. The method of claim 1, further comprising the following steps:
selecting a first granulometry of the abrasive cleaning material to be used;
emitting the abrasive cleaning material with the first granulometry;
selecting a second granulometry of the abrasive cleaning material to be used; and
emitting the abrasive cleaning material with the second granulometry,
wherein the steps of emitting the first granulometry and the second granulometry are performed in series or in parallel.

* * * * *